(12) United States Patent
Engelmann

(10) Patent No.: US 7,642,046 B2
(45) Date of Patent: Jan. 5, 2010

(54) METHOD FOR MONITORING RECRUITMENT OF PROTEINS TO THE INTRACELLULAR DOMAIN OF A RECEPTOR IN INTACT CELLS

(75) Inventor: Hartmut Engelmann, Roemerfeld 2, Neubiberg (DE) 85579

(73) Assignee: Hartmut Engelmann, Neubiberg (DE)

( * ) Notice: Subject to any disclaimer, the term of this patent is extended or adjusted under 35 U.S.C. 154(b) by 258 days.

(21) Appl. No.: 10/492,520

(22) PCT Filed: Oct. 14, 2002

(86) PCT No.: PCT/IL01/00828

§ 371 (c)(1),
(2), (4) Date: Oct. 4, 2004

(87) PCT Pub. No.: WO03/034073

PCT Pub. Date: Apr. 24, 2003

(65) Prior Publication Data

US 2006/0240483 A1    Oct. 26, 2006

(30) Foreign Application Priority Data

Oct. 14, 2001   (IL) .................................... 145918

(51) Int. Cl.
*C12Q 1/00* (2006.01)
*G01N 33/53* (2006.01)
*G01N 33/68* (2006.01)

(52) U.S. Cl. .............. 435/4; 435/7.1; 435/7.2
(58) Field of Classification Search ........ None
See application file for complete search history.

(56) References Cited

U.S. PATENT DOCUMENTS 6,294,348 B1 * 9/2001 Goeddel et al. ............ 435/7.23

FOREIGN PATENT DOCUMENTS

JP          10512443          12/1998

WO          9620723 A1        7/1996

OTHER PUBLICATIONS

Hu et al., A novel Ring finger protein interacts with the cytoplasmic domain of CD40. J. Biol. Chem. 269:30069-30072, 1994.*
Pullen et al., CD40-tumor necrosis factor receptor-associated factor (TRAF) interactions: regulation of CD40 signaling through multiple TRAF binding sites and TRAF hetero-oligomerization. Biochemistry. 37(34):11836-11845, 1998.*
Kuhne et al., Assembly and regulation of the CD40 receptor complex in human B cells. J. Exp. Med. 186:337-342, 1997.*
Crowther et al., ELISA. Theory and practice. Methods in Molecular Biology. pp. 35-61, 1995.*
Eliopoulos Aristides G et al "Epstein-Barr virus-encoded latent membrane protein 1 activates the JNK pathway through its extreme C terminus via a mechanism involving TRADD and TRAF2" Journal of Virology, vol. 73, No. 2 Feb. 1999 pp. 1023-1035.
Gires Olivier et al "Latent membrane protein 1 of Epstein-Barr virus interacts with JAK3 and activates STAT proteins" EMBO (European Molecular Biology Organization) Journal, vol. 18, No. 11 Jun. 1, 1999 pp. 3071.
Kieser Arnd et al "LMP1 signal transduction differs substantially from TNF receptor 1 signaling in the molecular functions of TRADD and TRAF2" EMBO (European Molecular Biology Organization) Journal, vol. 18, No. 9, May 4, 1999 pp. 2511-2521.
Schultheiss Ute et al "TRAF6 is a critical mediator of signal transduction by the viral oncogene latent membrane protein 1" EMBO (European Molecular Biology Organization) Journal, vol. 20, No. 20 Oct. 15, 2001 pp. 5678-5691.

* cited by examiner

*Primary Examiner*—Ruixiang Li
(74) *Attorney, Agent, or Firm*—Browdy and Neimark, PLLC

(57) ABSTRACT

The present invention relates to an immunological method and kit for monitoring recruitment of a protein to the intracellular domain of a receptor in intact cells.

41 Claims, 9 Drawing Sheets

Figure 1A
Figure 1B
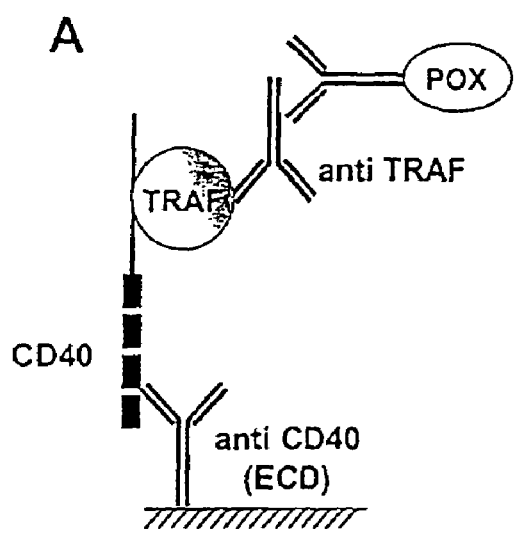
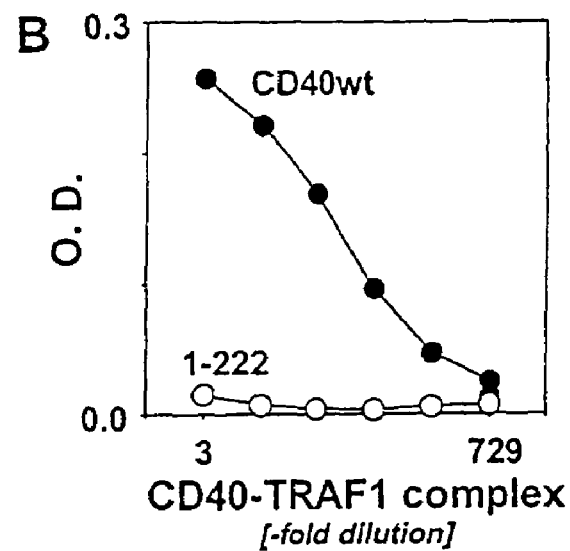

TRAF binding (fold of CD40 control)

Figure 5A
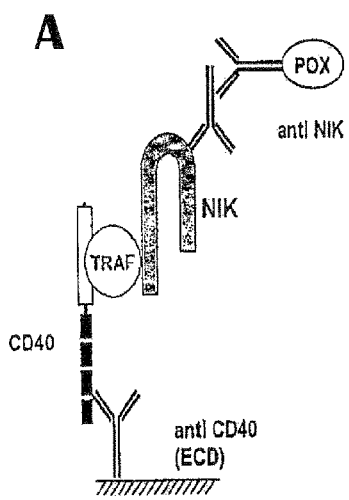
Figure 5B
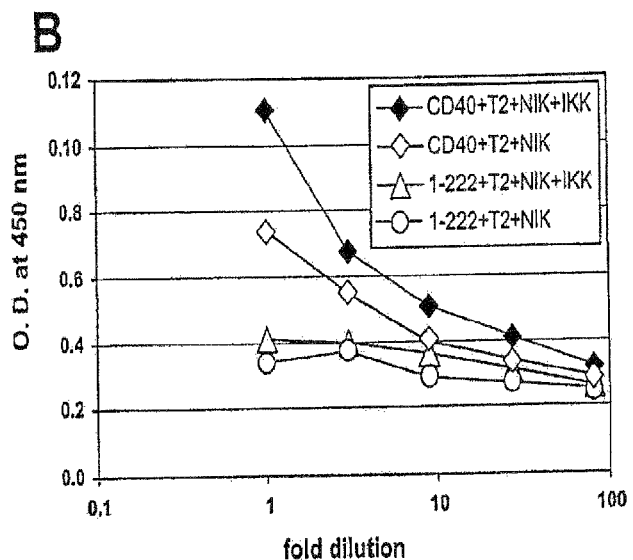
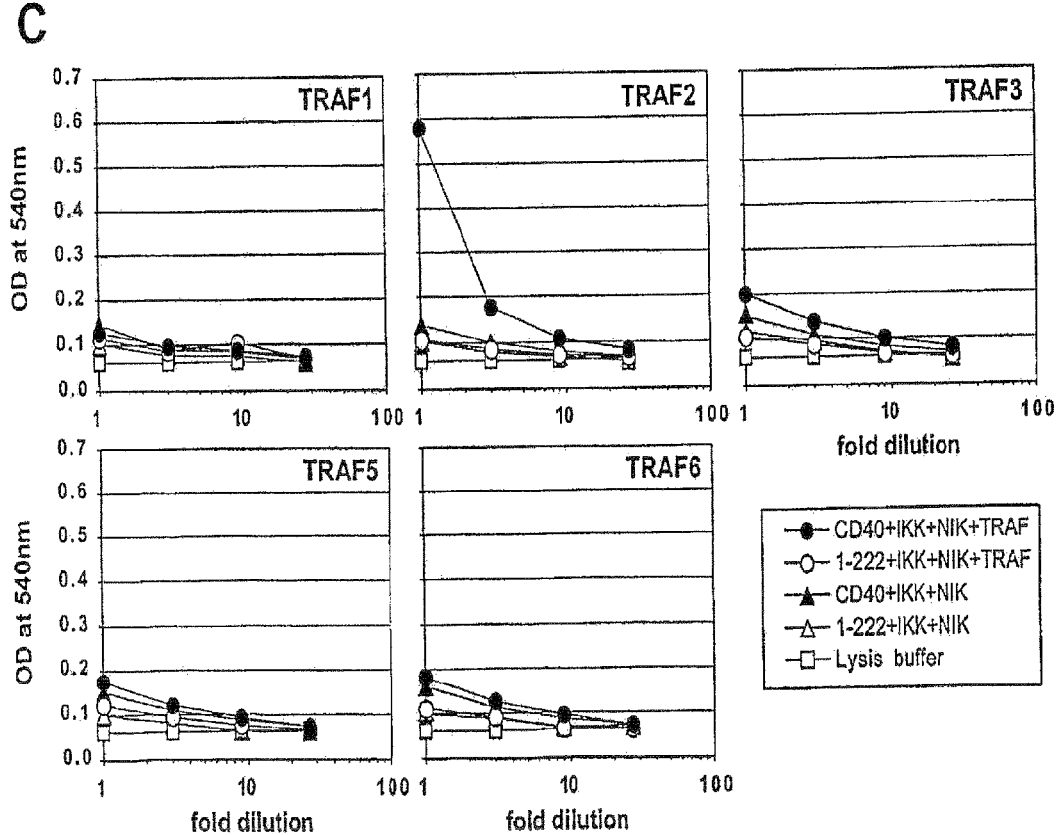
Figure 5C

* There is an ATG upstream of the Xba site.

METHOD FOR MONITORING RECRUITMENT OF PROTEINS TO THE INTRACELLULAR DOMAIN OF A RECEPTOR IN INTACT CELLS

FIELD OF THE INVENTION

The present invention relates to an immunological method and kit for monitoring recruitment of a protein to the intracellular domain of a receptor in intact cells.

BACKGROUND OF THE INVENTION

Cytokines mediate their effects by binding to specific receptors on their target cells. This interaction results in structural changes/modifications in the receptor's cytoplasmic part that eventually trigger intracellular signaling cascades. These signaling cascades usually include enzymes such as kinases, lipases or proteases that mediate the biochemical and genetic changes that are the basis for the biological response to a given cytokine.

As demonstrated for many cytokine receptors—such as the TNF receptor family—one of the first events after ligand binding to a receptor is the recruitment of various adaptor proteins to the signaling domain of the activated receptor (reviewed by Wallach et al. 1999 and Inoue et al. 2000). In a second step, these adaptor proteins mediate specific binding and activation of key enzymes constituting the various signaling cascades. The resulting multi-protein complex consisting of the receptor, and one or various signaling proteins was dubbed "signalosome". The composition of the signalosome essentially determines which combination of signal pathways is activated in the target cell. The signalosome may therefore be regarded as the central molecular switchboard that determines the eventual biological response to a cytokine.

In view of this molecular mechanism of cytokine receptor signal transduction, it becomes very important to understand the signalosome composition for a given receptor. Knowing the identity of the bound adaptor proteins, the circumstances under which they bind as well as their binding kinetics would allow predictions on the signals initiated by the receptor of interest. Such knowledge would make it also possible to relate signal-cascades or even combinations thereof to biological responses.

CD40, a member of the TNF receptor (TNFR) family, is recognized as the central switch point for the initiation of the interaction between antigen presenting cells (APC) and T-lymphocytes. By influencing basic functions such as cell proliferation, activation and apoptosis this receptor coordinates T-cell priming, the selection process for antibody producing B-cells as well as the activation of the effector mechanisms in macrophages to eliminate intracellular pathogens (reviewed in Grewal et al. 1998, Schonbeck et al. 2001). The importance of CD40 for the maturation and activation of diverse immune effector mechanisms becomes most obvious when this receptor or its ligand fail to function. In mammals this results in a condition known as Hyper IgM syndrome. This severe immune deficiency is characterized by high levels of plasma IgM and low levels of IgA, IgG, and IgE, the absence of germinal centers and the inability to mount a thymus dependent immune response (reviewed in Grewal et al. 1998, Ramesh et al. 1994). Further in vivo studies demonstrated that the CD40-CD40L receptor-ligand pair plays a primary role in the regulation of B-cell proliferation, immunoglobulin production, Ig class switching, rescue of B-cells from apoptosis, germinal center formation, the generation of B-cell memory and the regulation of inflammation (reviewed in Grewal et al. 1998, Schonbeck et al. 2001, Clark et al. 1996 and Foy et al. 1996). CD40's eminent role for the immune response led to the development of various therapeutic concepts in which unwanted immune reactions may be artificially suppressed (reviewed in Grewal et al. 1998 and Liu et al. 1996). It was found that the blockade of CD40-CD40L interactions might be useful for the treatment of autoimmune conditions, transplant rejection, graft versus host reaction and arteriosclerosis (Grewal et al. 1998 and Schonbeck et al. 2001). CD40 belongs to the group of TNF receptors that do not have a 'death domain'. They generate their signal through direct interaction with TNF receptor associated factors (TRAF) (reviewed in Arch et al. 1998 and Inoue et al. 2000).

TRAFs are a genetically conserved family of proteins that act as adaptors to recruit further signaling molecules such as the kinase NIK (Malinin et al. 1997), thereby activating important downstream effectors such as AP-1 and NF-κB. These transcription factors in turn have been shown to regulate numerous genes involved in various aspects of cellular and immune functions (reviewed in Baeurle et al. 1994, Ghosh et al. 1998 and Karin et al. 1997). Six TRAF proteins are known to date. The first two TRAF1 and TRAF2 were isolated as p75TNF receptor binding proteins (Rothe et al. 1994). All TRAF proteins share a common structural organization. A C-terminal interaction domain, dubbed TRAF domain, mediates the recruitment to various receptors of the TNFR family (Rothe et al. 1995). This domain also mediates homo and hetero-oligomerization and binding to other signaling molecules such as the death domain protein TRADD (reviewed in Arch et al. 1998 and Inoue et al. 2000). The TRAF domain is also the region of highest homology between the different TRAF family members. All TRAFs except TRAF1 have up to 6 repetitive Zn-finger motifs and one ring-finger motif in the N-terminal part that are essential for the activation of downstream components in the signaling pathway such as NIK or JNK (Malinin et al. 1997, Takeuchi et al. 1996, Liu et al. 1996 and Song et al. 1997). In addition TRAF3 and TRAF5 contain a coiled coil structure, which allows homo- and heteromerization between these two TRAFs (Pullen et al. 1998 and Leo et al 1999). Recent crystallization studies have demonstrated that TRAFs interact with their receptors as trimers (McWhirter et al. 1999, Park et al. 1999, Ye et al. 1999 and Ni et al. 2000). The recruitment is most likely achieved by ligand induced receptor trimerization, which results in the approximation of possible interaction sites and thus forming an optimal binding site for the trimeric TRAFs (Baud et al. 1999, Pullen et al. 1999). In view of the multitude of receptors that generate their signals through TRAF proteins it is not surprising that the disruption of TRAF genes in vivo has dramatic consequences. In mice TRAF2-, TRAF3- and TRAF6-deficiencies are lethal (Yeh et al. 1997, Nguyen et al. 1999, Xu et al. 1996, Lomaga et al. 1999 and Naito et al. 1999). A TRAF5 deficiency results in signaling defects for multiple receptors including CD27, CD30, CD40 and the LTJ3 receptor (Nakano et al. 1999). TRAF4 deficient mice are born with a tracheal malformation but no other obvious defects (Shiels et al. 2000). TRAF1 gene targeted mice have not been described.

Despite its relatively short signaling domain of 62 amino acids, CD40 was shown to interact with all TRAFs except TRAF4 (Pullen et al. 1998, Hu et al. 1994, Rothe et al. 1995, Mosialos et al. 1995, Cheng et al. 1995, Ishida et al. b 1996, Ishida et al. a 1996 and Krajewska et al. 1998). On the basis of sequence comparison between TRAF binding receptors two amino-acids sequence motifs were defined as minimal TRAF binding sites: PxQxT for TRAF1, 2 and 3 (Pullen et al. 1998, Cheng et al. 1996, Gedrich et al. 1996, Devergne et al. 1996, Boucher et al. 1997, Eliopoulos et al. 1997 Sandberg et al. 1997, Brodeur et al 1997 and Pullen et al. 1999) and basic-QxPxEx-acidic for TRAF6 (Pullen et al. 1999, Tsukamoto et al. 1999 and Darnay et al. 1999). TRAF5 appears to bind indirectly via TRAF3 (Pullen et al. 1999, Leo et al. 1999). Further refinement of the TRAF2 binding motif to the minimal consensus sequence P/S/T/AxQ/EE was achieved by crystallization studies (Ye et al. 1999). Both TRAF binding motifs are present in CD40 and have been shown to mediate TRAF recruitment to this receptor. Despite extensive structural studies on the CD40-TRAF interactions some basic questions concerning the assembly of the CD40-TRAF signalosome remain unresolved. It is still unclear whether and how the sequence context of the full length CD40 cytoplasmic domain influences the function of the two known TRAF binding motifs. It is also unknown whether the various components in the signalosome mutually affect binding to the receptor, for example by providing additional binding sites for the other signalosome proteins. Resolving these questions will not only be important in order to understand the signaling mechanisms of TRAF binding receptors but also for the rational design of drugs that interfere specifically with TRAF mediated signaling.

A protein designated NIK, including isoforms, analogs, fragments or derivatives thereof which are capable of binding to the tumor necrosis factor receptor-associated (TRAF) proteins is known (Malinin et al. 1997). As the TRAF proteins are involved in the modulation of mediation of the activation of the transcription factor NF-κB, which is initiated by some of the TNF/NGF receptors, as well as others, NIK and its isoforms etc. by binding to TRAF proteins is therefore capable of affecting (modulating or mediating) the intracellular signaling processes initiated by various ligands (e.g. TNF and others) binding to their receptors such as, for example, their modulation/mediation of NF-κB activation, via interaction directly or indirectly with TRAF proteins.

The interaction of cytokine receptors with their signal adaptor proteins was well studied for the TNF receptor gene family. Most assay systems use peptide fragments of the signaling domain of the receptor of interest and test the interaction of this peptide with known adaptor molecules under in-vitro conditions (Rothe et al. 1994, Hu et al. 1994 Boldin et al. 1995, Stanger et al 1995, Chinnaiyan, A. M. et al. 1995, Cheng, G. et al. 1995, Mosialos et al. 1995, Ishida, T et al. a, 1996, Ishida, T. b 1996 and Fields, S. 1989). The systems used comprise the yeast-two-hybrid-system (Fields et al. 1989), immuno-precipitation methods e.g. with Glutathion-S-transferase-tagged receptor fragments (Rothe at all. 1994, Boldin et al. 1995 Chinnaiyan et al. 1995 and Mosialos et al. 1995) or binding of labeled adaptor proteins to peptide receptor fragments spotted on filters (Boucher et al. 1997, Pullen et al. 1998; and Pullen et al. 1999). A common problem of all these methods is that the signalosome assembly occurs not in its natural "juxta-membrane" cellular environment.

A need therefore exists for a simple quantitative assay in which the signalosome assembly occurs in its natural cellular environment as opposed to conventional in vitro conditions.

Immunologic methods for quantifying antigens provide excellent sensitivity and specificity and have become standard techniques for both research and clinical applications. All modern immunochemical methods of protein quantitation are based upon a simple and accurate method for measuring the quantity of an indicator molecule (antigen or antibody) that binds to solid surfaces, such as plastics, and by washing away indicators not bound.

When the indicator molecule is labeled with a radioisotope, the assay is called a radioimmunoassay. The indicator molecule is quantified by counting radioactive decay events in a scintillation counter. The assay is called an Enzyme Linked Immunoadsorbent Assay (ELISA), when the indicator molecule is covalently coupled to an enzyme which can cleave a reporter substrate, which may be colorimetric, chemiluminescent, fluorometric, or phosphometric. The indicator molecule may be quantified by determining with a spectrophotometer the initial rate at which the enzyme converts a neutral substrate to a colored or emitting product.

ELISAs may be classified under four headings: direct, indirect, sandwich and competitive (Crowther, J. R. (1995) Methods in Molecular Biology volume 42 pages 35-50). In the direct-labelled antigen ELISA, the antibodies are adsorbed to the solid-phase and the antigen is labelled. In the direct-labelled antibody ELISA, the antigen that is attached to the solid phase is reacted directly with an enzyme labelled antibody (e.g. conjugated with an enzyme). In the indirect ELISA, the antibody is not labelled and a second antispecies specific antibody conjugated to an enzyme is used.

In the direct-sandwich ELISA, first antibody is attached to the solid phase, the tested antigen can be added and captured by the attached antibody. A second different antibody, conjugated to an enzyme is used to detect the captured antigen. In the indirect-sandwich ELISA the second antibody is not labeled, it is generated in different animal species than the first one, and it is detected by a third antispecies specific labeled antibody.

Competitive ELISA consists of two reactants, which are competing for a third one. The following are examples of competitive ELISAs:

In the direct labelled-antibody-competitive ELISA, the antigen is adsorbed to the solid phase and a pre-titrated conjugated antibody is added, so that the antigen is saturated and no free recognition sites are available for further antibody combination. The interaction of antigen and conjugated antibody is perturbed if the labelled antibody is mixed with another antibody (competing antibody) that is able to react with the solid phase-bound antigen. Such an assay can be used to compare monoclonal antibodies directed against the same protein.

In the direct-antigen-competitive ELISA, the antigen is adsorbed to the solid phase and a pre-titrated conjugated antibody is added so that the antigen is saturated and no free antigenic sites are available for further antibody combination. In this case the interaction of antigen and conjugated antibody is perturbed if the labelled antibody is mixed in with another antigen (competitor). Thus, if the competitor antigen is cross-reactive, the labelled antibody is unavailable to react with the antigen attached to the solid phase, and a reduction in the colour is observed. Such assays are used to quantify antigens or to compare the relative affinity of binding of two antigens for the same antibody.

In the indirect-antigen/antibody-competitive ELISA, the antibody is not labelled and it is detected by a third anti species-specific labelled antibody.

Currently no general, sensitive, specific, easy to perform and efficient method exists which allows quantitation of recruitment of various adaptor proteins to the signaling domain of the activated receptor in intact cells. Therefore the immunologic method described in the present invention solves a long-standing problem in the area of signal transduction.

SUMMARY OF THE INVENTION

The present invention relates to a method for monitoring binding of a protein such as TRAF1, TRAF2, TRAF3, TRAF4, TRAF5, TRAF6, NIK and IKK to the intracellular domain of a receptor such as CD40, BCMA, LTβR-receptor, TACI, p75TNFR and CD27, in it cell comprising:

c) inducing signalosome formation in cells,
d) lysing the cells,
c) incubating the cell lysate on a solid phase coated with a first antibody capable of capturing the receptor within the signalosome,
d) separating the solid phase from the cell lysate, and
e) detecting and measuring the amount of the protein bound to the solid phase using a second antibody capable of detecting the protein.

More specifically, the signalosome formation according to the method of the invention may be induced e.g. by receptor overexpression, by treating with the receptor specific ligand or by receptor cross-linking, e.g. by a specific antibody. The receptor may be fused to a polypeptide e.g. the extracellular domain of CD40, or peptide, such as a tag e.g. histidine, FLAG, VSV-G, Protein-C and c-myc tags, at its extracellular domain and thus, the first antibody is specific for such fused polypeptide or peptide. Also, the binding protein or signalosome component measured, may be fused to a polypeptide tag and thus, the second antibody is specific to such a tag.

In one aspect, the invention relates to methods for screening for a molecule e.g. synthetic organic compound, which inhibit the binding of an adaptor protein and/or signaling protein to an intracellular domain of a receptor or which inhibit signalosome assembly in a cell comprising:

exposing the cells to individual molecules, monitoring binding of a protein to the intracellular domain of a receptor or signalosome assembly and then selecting a molecule capable of inhibiting the binding of the adaptor and/or signalling protein to the receptor or signalosome assembly. The invention also provides the molecules selected by the screening methods of the invention.

The invention further provides a kit for measuring and quantitating binding of an adaptor and/or signaling protein to a specific membrane protein in a cell comprising:

a) expression plasmids for the overexpression of the membrane protein fused to a first tag or to a polypeptide and a for the expression of adaptor/signalling protein fused to a second tag.
b) ELISA microtiter plates coated with a first antibody capable of binding the first tag or polypeptide fused to the membrane protein,
c) A second antibody capable of binding the second tag fused to the adaptor/signalling protein.
d) HEK293 cells
e) Transfection reagents
f) Lysis buffer
e) a protocol describing concentration of vectors in the transfection reaction, and concentration of antibodies in the ELISA and way of quantitation.

BRIEF DESCRIPTION OF THE FIGURES

FIG. 1A is a schematic representation of the assay according to the invention for measuring the signalosome assembly for CD40. Antibodies against the extra-cellular domain of CD40 were adsorbed to a solid phase. Then the multi-protein complex consisting of CD40 and bound TRAF adaptor obtained from extracts of cells overexpressing CD40 and TRAF adaptor (for details see example 1) are captured in anti CD40 adsorbed solid phase. Bound TRAF is detected with specific horseradish peroxidase coupled (POX) antibodies against TRAF adaptor.

FIG. 1B shows the recruitment of TRAF1 to the CD40 receptor by the assay schematically represented and described in FIG. 1A. CD40 wt (closed circles) or CD40 1-222 (open circles) were co-expressed with TRAF1 in HEK 293T cells as described in example 1. After 27 hours, the cells were detergent lysed, the lysates cleared by centrifugation diluted by serial 3 fold dilutions and incubated With anti CD40 adsorbed microtiter plates. CD40 bound TRAF1 was detected at the indicated dilutions with a commercially available antibody against TRAF1 and a seconday antispecies anti-IgG antibody horseradish peroxidase coupled (POX). (For details on antibodies used see Table 1).

FIG. 5A is a schematic representation of the recruitment assay in intact cells according to the invention for monitoring the recruitment of signal proteins mediated via an adaptor protein. This is demonstrated with the kinase NIK that is recruited to CD40 via TRAF. Following co-transfection of three expression plasmids encoding for CD40, TRAF2 (T2) and NIK into 293T the cells are lysed and CD40 bound NIK was determined as described in example 7.

FIG. 5B shows the results obtained with the assay schematically represented and described in FIG. 5A. Combinations of indicated expression plasmids were over-expressed in 293T cells as described in example 7. Cells were extracted and CD40 bound NIK was determined as described in example 7. The assay background was determined by co-transfection of a CD40 mutant that lacks the entire signalling domain (1-222). This figure shows also the effect of IKKα overexpression on NIK recruitment.

FIG. 5C shows that NIK recruitment to CD40 is TRAF2 dependent. The indicated plasmid combinations were transfected as described in example 7. CD40 bound NIK was determined by ELISA as described in example 7).

DETAILED DESCRIPTION OF THE INVENTION

Figure 2A:
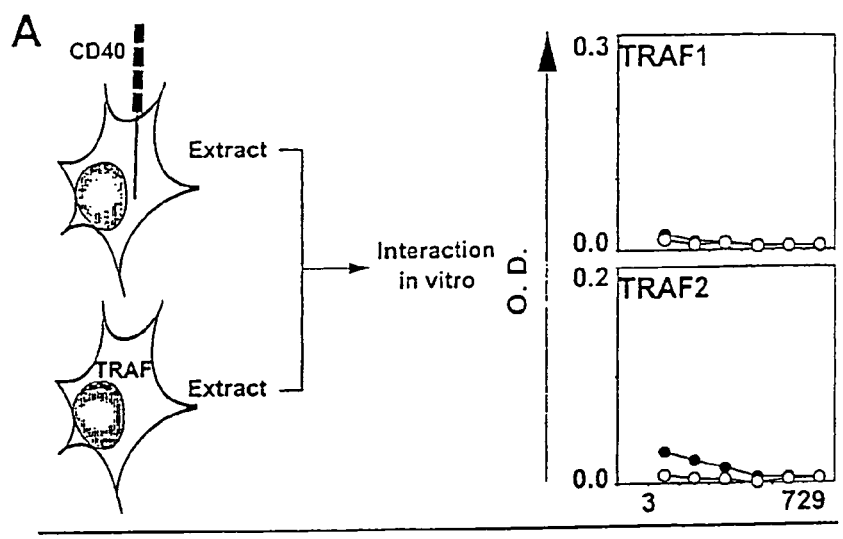
FIG. 2 shows the comparison of recuitment of TRAF1 and TRAF2 to the CD40 receptor in intact cells versus cell extracts. CD40 wt (closed circles) or the signal domain deficient mutant CD40 1-222 (open circles) were either expressed separately (A) or co-expressed with TRAF1 or TRAF2 (B) in 293T cells. After 27 hours, the cells were detergent lysed as described in example 1. The extracts from 293T cells expressing only CD40 wt, or CD40 1-222 were mixed at a 1:1 ratio with extracts from TRAF1 or TRAF2 expressing 293T cells and incubated over night at 4° C. All other extracts were kept under identical conditions. CD40 bound TRAF was measured at the indicated dilutions of the cell extracts by ELISA as described in example 1. The assays were done with antibodies listed in Table 1. For determination of TRAF2 a monoclonal rat anti TRAF2 (clone 8.F1; kindly provided by Dr. E. Kremmer, GSF, Institut fuer Molekulare Immunologie; Marchioninistr. 25,81337 Munchen) was used as detection antibody (hybridoma supernatant diluted 1:10).

The invention relates to a sensitive assay which allows monitoring the recruitment of a protein to the intracellular domain of a receptor of interest in an intact cell. The term intact cell refers to a cell that has not been lysed and therefore recruitment, as opposed to conventional assays, is carried out in its natural cellular environment.

The terms recruitment of a protein to the intracellular domain of a receptor and binding of a protein to the intracellular receptor are interchangeable.

The terms recruitment of a protein to the signalosome or binding of a protein to the signalosome are also interchangeable.

The terms factor polypeptide and protein are interchangeable.

As demonstrated for many cytokine receptors—such as the TNF receptor family—one of the first events after ligand binding to a receptor is the recruitment of various adaptor proteins to the signaling domain of the activated receptor (reviewed by Wallach et al. 1999 and Inoue et al. 2000). In a second step, these adaptor proteins mediate specific binding and activation of key enzymes or signaling proteins constituting the various signaling cascades. The resulting multiprotein complex comprising of the receptor and one or more adaptors and one or more signaling proteins was named "signalosome". The composition of the signalosome essentially determines which combination of signal pathways is activated in the target cell. The signalosome may therefore be regarded as the central molecular switchboard that determines the eventual biological response to a cytokine.

In view of this molecular mechanism of cytokine receptor signal transduction, it becomes very important to understand the signalosome composition for a given receptor. Knowing the identity of the bound adaptor proteins, the circumstances under which they bind as well as their binding kinetics would allow predictions on the signals initiated by the receptor of interest. Such knowledge would make it also possible to relate signal-cascades or even combinations thereof to biological responses.

This method is suitable for screening for compounds (molecules) that interfere specifically with the integration of defined proteins into the signalosomes. This method is especially suitable for screening of compounds that interfere specifically with the integration of key enzymes constituting the various signaling cascades e.g kinases, lipases or proteases, in the signalosome. Such compounds could be very useful as drugs to decouple a receptor of interest from only one signal pathway with unwanted effects, leaving other beneficial functions of the same receptor intact.

The recruited protein can be an adaptor protein or signaling protein such as key enzymes constituting the various signaling cascade e.g. NIK, IKK etc. The receptors can be any receptor to which proteins are recruited, for example receptors of the TNF/NGF family.

The present invention also includes, in addition to the full proteins also fragments thereof e.g. instead of the whole membrane protein, employing e.g. the membrane and intracellular domain and instead of the whole adaptor/signaling protein, employing only the signalosome binding domain.

This assay, inter alia, can be used for analysis of signalosome composition, important sites for protein interactions, drug high throughput screening, and the like.

In general, the assay according to the invention can be can be used to monitor association or recruitment of an adaptor or signalling protein to the intracellular domain of a receptor occurring inside the cells e.g. this assay can be used to monitor recruitment of any TNF/NGF receptor associated proteins, such as TRAF1, TRAF2, TRAF3, TRAF4, TRAF5 and TRAF6 or fragments thereof. The recruitment can be measured in cells, which express high amounts of the receptor and recruited proteins.

Signalosome formation can be induced by either overexpression of receptors, such as CD40 and/or adaptors such as TRAFs- and/or signalling proteins such as NIK, IKK etc. equivalent thereof or fragment thereof; or by activation of receptors by ligand triggering or by receptor cross-linkage. Receptor activation may be achieved by cross-linking receptors with specific antibodies (see Engelmann et al. 1990). In the following non-limiting examples, signalosome formation or recruitment is induced by overexpression of CD40, TRAF, NIK and equivalents.

The receptor and recruitable proteins can be over expressed by transfection with expression vectors encoding said proteins. The receptor and the recruited proteins may be encoded in different plasmids or may be linked in one plasmid. The increased expression of the receptor and recruited proteins can be transient or constitutive by using appropriate expression systems and resistance markers known in the art.

Overexpression by the use of a vector for inducing and/or enhancing the endogenous production of the receptor and recruited proteins is also contemplated according to the invention. The vector may comprise regulatory sequences functional in the cells desired to express the receptor and/or the recruited proteins, e.g. such regulatory sequences may be promoters or enhancers. The regulatory sequence may then be introduced into the right locus of the genome by homologous recombination, thus operably linking the regulatory sequence with the gene, the expression of which is required to be induced or enhanced. The technology is usually referred to as "endogenous gene activation" (EGA), and it is described e.g. in WO 91/09955.

Transfection of the plasmid can be carried out by any method known in the art e.g. by the calcium phosphate method (Kingston et al. 1993).

Measurements of recruitment of proteins to a given receptor can be tested by the "recruitment assay in intact cells" in any cell e.g. HEK293, 293T cells and B cells in which the consequences of signalling can be assessed.

For the assay e.g. $2\times10^5$ cells can be seeded into 3.5 cm dishes grown about 16 hours at 37° C. and transfected with expression plasmid encoding the receptor e.g. CD40 and an expression plasmid encoding one or more recruitable proteins/peptides e.g. TRAF, NIK. About twenty-seven hours after transfection, the cells are detached, washed and detergent extracted e.g. with lysis buffer comprising phosphate buffered saline (PBS) containing a protease inhibitor cocktail (0.16 mM Pefabloc, 105 IU Aprotinin), 1% Triton X100 and 0.1% Na Azide.

The lysates are cleared by centrifugation in a micro-centrifuge, diluted preferably to 3 fold serial dilutions and then every diluted sample incubated for about 2 hours (or overnight) in a solid phase, preferably wells of ELISA microtiter plates, coated with a mAb specific to the receptor extracellular domain e.g. (Ro1 for CD40) (Schwabe et al. 1997). In order to increase the sensitivity of the assay the anti receptor antibody can be coated to the solid phase trough an anti species-specific antibody. For control purposes, instead of the plasmid encoding the wild type receptor, a plasmid encoding a receptor mutant lacking the entire or part of the signalling domain can be used for transfection. Following incubation, washes will be preferably carried out to remove unbound protein. To detect recruited proteins, specific antibodies to said recruited protein, e.g. anti TRAF, anti NIK, of interest are loaded into the plates, incubated for about 3 hours at room temperature and followed by washes to remove unbound antibody. This antibody can be detected by using enzyme-linked antibody or enzyme-linked secondary anti species IgG antibody or protein A/G and visualized by coloured, florescent or chemiluminescent specific substrates. Alternatively, the antibody or protein A/G may be radioactively labelled. In addition, biotin may be chemically linked to the antibody or protein A/G trough lysine residues. Labelled streptavidine may be used to detect the presence of biotin.

The recruited protein can be quantitatively measured using the recruitment assay carried out in intact cells. For that purpose, the assay conditions are adjusted in such a way that the recruitable protein is in significant excess over the receptor protein. Therefore a concentration of recruited protein over receptor concentration in the cell should preferably be equal or above 2. This ratio can be achieved by carrying out the transfections with increasing amount of plasmid encoding the recruited protein over the amount of the plasmid encoding the receptor and or by using more potent promoters controlling the transcription of the respective proteins.

The recruited protein concentration can be measured using a reference cell extract containing e.g. 1000 U/ml of receptor/recruited protein complexes as a standard in each assay. This standard extract will preferably consist of a large pool of cell extracts from cells that were co-transfected with the plasmids encoding for the recruited protein of interest and the receptor of interest. The extracts are frozen in small aliquots and kept at −80° C. until further use. By comparing levels of unknown samples to these extracts, it is possible to determine the relative receptor-recruited protein complex concentrations in arbitrary units. The following formula can be used for quantitation and the necessary normalization for sample-to-sample variations in the receptor expression:

$$\frac{[\text{receptor-recruited protein complex}](arb.\ \text{Units/ml})}{[\text{receptor concentration}](ng/\text{ml})} = \text{receptor}$$

recruited protein complex per receptor protein $(arb.\ \text{Units}/ng)$.

The receptor concentrations can be determined with an ELISA employing a monoclonal and a polyclonal anti receptor antibody, both specific for the extracellular domain of said receptor. A purified soluble extra cellular domain can be used as a standard.

In a non limiting example, the assay was shown to be suitable for measuring recruitment of signal proteins, e.g. NIK (a downstream mediator in the NF-κB pathway Malinin et al. 1997) to a cytokine receptor, e.g. CD40 via an adaptor protein e.g. TRAF2. The recruitment of NIK to CD40 was TRAF2 dependent and improved when IKK was co-expressed.

The receptor can be expressed as a fusion protein in which the extracellular portion of the receptor is fused to a polypeptide tag e.g. histidine tag. Using this fusion protein allows monitoring the recruitment to any receptor by using tag specific antibodies e.g. anti histidine tag, to immobilize the receptor to the solid phase without the need of receptor specific antibodies. Expression vectors designed for the production of tag fusion proteins are commercially available. These vectors encode a specific tag up-stream or down-stream of the cloning site. Alternatively, the tag may be fused to the gene of interest by PCR, for example by including the tag sequence in the primers used for the amplification of the DNA of interest. The PCR amplified DNA fusion product may be cloned into an expression vector comprising appropriate regulatory signals for transcription and translation.

Examples of epitope tags are histidine tags (a stretch of 6 consecutive histidines, Janknecht et al. 1991), FLAG (8 amino acid epitope ROCHE), VSV-G (11 amino acid epitope from vesicular stomatitis virus ROCHE), Protein-C (12 amino acid epitope from the heavy chain of human Protein C, ROCHE), and c-myc (10 amino acid epitope from the human c-myc gene protein ROCHE). In an epitope tagged protein the added sequence is a short peptide of about 3-12 amino acids, usually with no function of its own. The important property of the epitope tag is its ability to be recognized and bound by a single, tag-specific antibody. Epitope tags can be placed e.g. at the amino-terminus (N-terminus).

A wide range of epitopes has been used to tag proteins and many tag specific antibodies are commercially available. The best epitope tag for a particular experimental system is the one that does not interfere with the function or cellular processing of the tagged protein, yet generates a strong detection signal on Western blots, in immunofluorescence microscopy, or quantitative assays.

Alternatively, a hybrid construct comprising the extracellular domain of a given receptor such as CD40 and intracellular signalling domain of different receptors can be used in the recruitment assay carried out inside the cells. Hybrid receptor can be used to compare recruitment to a variety of intracellular receptors using the same capturing antibody e.g. CD40 specific antibodies. In a non limiting example presented the measurement of TRAF recruitment to the signalling domains of BCMA the LTβR-receptor TACI the p75TNFR or the CD27 was carried out by co-transfecting 293T cells with a plasmid encoding hybrid receptors together with a plasmid encoding TRAF and measurement of the TRAF/Receptor complex using the same ELISA sandwich. The assay described here allows for the first time the direct comparison of several receptors with respect to their binding characteristics for a given set of signal molecules e.g. TRAF. This will make it possible to draw conclusions as to the biological functions of a given TRAF receptor combination. The results obtained demonstrate again the feasibility of the recruitment assay for monitoring TRAF recruitment to any receptor.

The same approach can be adopted to detect recruited proteins, consisting of expressing the recruited proteins fused to a polypeptide Tag such as EK and detecting the recruited protein with commercially available Tag specific antibodies such as AntiXpress antibodies.

In a non limiting example below it has been demonstrated the recruitment of tagged dTRAF6 to CD40 by using an antibody specific to EK (antiexpress antibody) to monitor the recruited dTRAF6.

The results obtained suggest therefore that using this assay, recruitment of any TRAF to any receptor can be specifically monitored.

In the non-limiting examples presented below, the recruitment assay based on protein recruitment to a receptor in the intracellular environment, has been demonstrated to be more sensitive than the conventional recruitment assay (FIG. 2). In addition it has been demonstrated that recruitment is dependent on Multiple interactions sites either provided by the receptor itself or by as yet unidentified molecules in the signalosome. For example the assay allows a more precise determination of the structural requirements that determine TRAF binding to CD40 e.g. the necessity of the intact CD40 C-terminus. Furthermore it was possible to demonstrate how different TRAFs affect each others binding. The recruitment assay according to the invention is quantitative sensitive and suitable for monitoring recruitment of various different adaptors and/or signaling proteins to any receptor. In view of these findings it is expected that the described assay method will contribute greatly to the understanding of the interaction between a cytokine receptor and intracellular signalling molecules. This knowledge will essential for the rational development of drugs that act on the level of signalosome assembly.

The recruitment assay according to the invention can therefore be used to screen for potential therapeutically valuable molecules which inhibit recruitment of adaptor and/or signaling proteins to the intracellular domain of a receptor or which inhibit signalosome formation. Cells can be exposed to a variety of individual synthetic organic compounds created by combinatorial chemistry and recruitment in treated cells versus control cells can be monitored and quantited by the recruitment assay according to the invention. The compounds tested may be obtained not only through combinatorial chemistry, but also from other high throughput synthesis methods. Automated techniques enable the rapid synthesis of libraries of molecules, large collections of discrete compounds, which can be screened. Producing larger and more diverse compound libraries increases the likelihood of discovering a useful drug within the library. For high throughput screening robots can be used to test inhibition of recruitment or disruption of signalosome formation by thousands of compounds.

The invention also provides a kit for the measurement and quantitation of protein recruitment to specific receptors comprising the following components:

a) two expression plasmids, one for the overexpression of the membrane protein fused to a first tag or to the extracellular domain of the CD40 receptor, and the other plasmid for the expression of an adaptor/signalling protein fused to a second tag.

b) ELISA microtiter plates coated with a first antibody capable of binding a first tag or to the CD40 extracellular domain fused to the membrane protein, c) a second antibody capable of binding 'too ' a second tag fused to the adaptor/signalling protein.

d) Transfection reagents e) Lysis buffer e) a protocol describing concentration of vectors in the transfection reaction, and concentration of antibodies in the ELISA and way of quantitation.

Such a kit can be used for selecting molecules capable of inhibiting recruitment, or inhibiting binding of an intracellular protein to the intracellular domain of a receptor, or molecules capable of inhibiting signalosome formation. For example, the cDNA or genomic DNA encoding the receptor can be introduced in one vector and the cDNA or genomic DNA encoding the adaptor/signalling protein can be introduced in the other vector provided by the kit, using recombinant techniques well known in the art. The vectors provided in the kit are such, that one allows expression of fusion proteins comprising the membrane protein encoded by the cDNA or genomic DNAs fused to a first tag or to the extracellular domain of CD40 and the other plasmid allows expression of adaptor or signalling domain fused to a second tag. Cells e.g HEK293 are transfected with a mixture of both vectors at appropriated ratio (see above), using the provided transfection reagents and the transfected cells are incubated with individual molecules e.g. synthetic organic molecules. After 27 hours, the cells are detergent lysed, the lysates cleared by centrifugation, diluted by serial 3 fold dilutions and incubated with antibodies directed to the first tag or anti CD40 adsorbed microtiter plates. After extensive washes which remove non bound proteins, bound proteins can be detected with the antibody against the second tag and a seconday antispecies anti-IgG antibody horseradish peroxidase coupled. The level of the recruited protein can be measured as described above and the effect of every single molecule on this recruitment can be compared to a control sample of cells incubated in growth medium or buffer alone.

The invention will now be illustrated by the following non-limiting examples:

EXAMPLES

Example 1

Monitoring TRAF1 Recruitment to CD40 in Intact Cells.

In order monitor TNF receptor associated factor 1 (TRAF1) recruitment to the CD40 receptor, in intact cells, CD40 and TRAF1 encoding plasmids generated as described in example 7) were used to co-transfect the human embryonic kidney 293T cells (HEK293 ATTC CRL-1573 over expressing the T antigen) (DuBridge et al 1987). $2\times10^5$ cells were seeded at into 3.5 cm dishes grown 16 hours at 37° C. and transfected with 1 μg CD40 expression plasmid and 2 μg of an expression plasmid encoding TRAF by the calcium phosphate method (Kingston et al. 1993). The two expression plasmids, TRAF1 plasmid and CD40 plasmid were used for transfection at a ratio greater than 2:1 respectively in order to saturate all the CD40 molecules produced. Twenty-seven hours after transfection, the cells were detached, washed once with ice cold phosphate buffered saline (PBS) and detergent extracted with 180 μl lysis buffer [phosphate buffered saline (PBS) containing a protease inhibitor cocktail (0.16 mM Pefabloc, 105 IU Aprotinin), 1% Triton X100 and 0.1% Na Azide]. Since CD40 has a tendency for ligand independent signaling when expressed at high levels it was not necessary to activate the receptor with DC40 ligand or mimetic anti CD40 antibodies before lysis. This feature is shared by various members of the TNFR gene family (Boldin et al. 1995, Siegel et al. 2000 and Chan et al. 2000).

The lysates were cleared by centrifugation at 15000 G at 4° C. in a micro-centrifuge, 3 fold serially diluted (with lysis buffer containing 1% bovine serum albumin) and then every diluted sample incubated for 2 hours at room temperature (or overnight) in wells of ELISA microtiter plates coated with a mAb (Ro1) specific to the CD40 extra-cellular domain (Schwabe et al. 1997). For control purposes, instead of the wild type CD40 plasmid, a plasmid encoding a CD40 mutant lacking the entire signaling domain was used for transfection and transient expression (CD401-222, FIG. 1B). Following incubation exhaustive washes were carried out on the microtiter plates to remove any unbound protein [about 10 washing steps with PBS containing 0.05% Tween 20) PBS/Tween)]. To detect bound TRAF1, anti TRAF1 specific antibodies were loaded into the plates, incubated for about 3 hours at room temperature, preceded by extensive washes to remove unbound antibody and detecting the bound antibody with an HRP conjugated secondary antibody. All antibodies (except when used as solid phase antibody) were diluted in PBS/Tween containing 1% BSA.

The result obtained using the above described assay, schematically represented in FIG. 1A demonstrate that recruitment of TRAF1 to the CD40 receptor occurring in intact cells can be detected (filled circles in FIG. 1B) and at very low protein concentration i.e. up to a 243-fold dilution of the original extract. Detection of TRAF1 recruitment to CD40 intracellular domain even under very low protein concentration indicates that this recruitment assay is highly sensitive. The high specificity of this assay was demonstrated in the experimental control group with a signalling-domain-deficient CD40 mutant (CD40-222) in which recruitment of TRAF1 is undetectable (open circles in FIG. 1B).

Recruitment of TRAF2, 3, 5 and 6 to CD40 is described in examples 4 and 5 below using different expression vectors (described in example 7) encoding either TRAF2, 3, 5 and 6 respectively instead of TRAF1. The antibodies used for the detection of the different TRAFs are described in Table 1.

Additional alternative antibodies tested in the recruitment assay are given in Table 2.

TABLE 1

| Recruitment assay for | Solid Phase antibody (at 5 μg/ml) | Sec. Capture antibody (when needed) | Min. initial dilution of lysate | Detection Ab (Dilution) | HRP-labeled secondary Ab (Producer) (Dilution) |
|---|---|---|---|---|---|
| TRAF1 to CD40 | Anti CD40 ECD (Ro1[1]) | | 1:3 | Rabbit anti TRAF1 (G-20; SC-983)[3] (1:1000) | Goat anti Rabbit IgG (H + L) (DIA)[6] 1:30 000 |
| TRAF2 to CD40 | Anti CD40 ECD (Ro1[1]) | | 1.3 | Rabbit anti TRAF2 (H-249; SC-7187)[3] (1:3000) | Goat anti Rabbit IgG (H + L) (DIA)[6] 1:30 000 |
| TRAF3 to CD40 | Anti CD40 ECD (Ro1[1]) | | 1:3 | Rabbit anti TRAF3 (BD/Pharm)[5] (1:5000) | Goat anti Rabbit IgG (H + L) (DIA)[6] (1:30 000) |
| deltaTRAF5(145-557)-His to CD40 | Donkey anti Rabbit Ig (DIA)[6] | Rabbit anti CD40[7] (1:10 000) | undiluted | AntiXpress (IV)[4] (1:1000) | Goat anti Mouse Ig (DIA)[6] (1:4000) |
| deltaTRAF6 (300-524)-His to CD40 | Donkey anti Rabbit Ig (DIA)[6] | Rabbit anti CD40[7] (1:10 000) | undiluted | AntiXpress (IV)[4] (1:1000) | Goat anti Mouse Ig (DIA)[6] (1:4000) |

[1]Ro1: see Schwabe, R. F., S. Hess, J. P. Johnson, and H. Engelmann. 1997. Modulation of soluble CD40 ligand bioactivity with anti-CD40 antibodies. Hybridoma 16: 217.
[2]Abbreviations: HRP: Horse radish Peroxidase; (H + L): (Heavy + Light) chain; ECD: extra-cellular Domain; His: Histidin-tagged
[3]SC: Santa Cruz Biotechnology, Inc., 89-2 Bergheimer Straβe, 69120 Heidelberg, Tel. 49 (0)6221 4503 0, Toll Free +800 4573 8000, FAX 49 (0)6221 4503 45
[4]IV: Invitrogen GmbH, Technologiepark Karlsruhe, Emmy-Noether Strasse 10, 76131 Karlsruhe, Phone: 0800-0 83 09 02, FAX: 0800-0 83 34 35
[5]BD/Pharm: Becton Dickinson Biosciences (Pharmingen Products), Tullastrasse 8-12, 69126 Heidelberg, Germany, Tel: +(49) 6221.305.0, Fax: +(49) 6221.305.216,
[6]DIA: Dianova, Gesellschaft für biochemische, immunologische und mikrobiologische Diagnostik mbH, Mittelweg 176, D-20148 Hamburg, Tel.: 040/4 50 67-0, Fax: 040/4 50 67-490.
[7]see Schwabe, R. F., H. Engelmann, S. Hess, and H. Fricke. 1999. Soluble CD40 in the serum of healthy donors, patients with chronic renal failure, haemodialysis and chronic ambulatory peritoneal dialysis (CAPD) patients. Clin. Exp. Immunol. 117: 153.

TABLE 2

| Recruitment assay for | Solid Phase antibody (at 5 μg/ml) | Sec. Capture antibody (when needed) | Min. initial dilution of lysate | Detection Ab (Dilution) | HRP-labeled secondary Ab (Producer) (Dilution) |
|---|---|---|---|---|---|
| TRAF1 to CD40 | Anti CD40 ECD (Ro1[1]) | | 1:3 | Rabbit anti TRAF1 (G-20 SC-983)[3] (1:1000) | Goat anti Rabbit IgG (H + L) (DIA)[6] 1:30 000 |
| deltaTRAF3 (89-567) to CD40 | Goat anti Rabbit Ig (DIA)[6] | Rabbit anti CD40[7] (1:10 000) | | AntiXpress (IV)[4] (1:1000) | Goat anti Mouse Ig (DIA)[6] (1:4000) |
| deltaTRAF3(324-567)-His to CD40 | Goat anti Rabbit Ig (DIA)[6] | Rabbit anti CD40[7] (1:10 000) | 1:3 | AntiXpress (IV)[4] (1:1000) | Goat anti Mouse Ig (DIA)[6] 1:4000) |
| TRAF5(21-557)-His to CD40 | Donkey anti Rabbit Ig (DIA)[6] | Rabbit anti CD40[7] (1:10 000) | undiluted | AntiXpress (IV)[4] (1:1000) | Goat anti Mouse Ig (DIA)[6] (1:4000) |
| TRAF6 to CD40 | Anti CD40 ECD (Ro1[1]) | | undiluted | Rabbit anti TRAF6 (H-274 SC-7221)[3] (1:1000) | Goat anti Rabbit IgG (H + L) (DIA) 1:30 000 |
| TRAF6 to CD40 | Anti CD40 ECD (Ro1[1]) | | undiluted | Goat anti TRAF6 (C-20 SC-6223)[3] (1:1000) | Rabbit anti Goat Ig (DIA)[6] (1:4000) |

[1]Ro1: see Schwabe, R. F., S. Hess, J. P. Johnson, and H. Engelmann. 1997. Modulation of soluble CD40 ligand bioactivity with anti-CD40 antibodies. Hybridoma 16: 217.
[2]Abbreviations: HRP: Horse radish Peroxidase; (H + L): (Heavy + Light) chain; ECD: extra-cellular Domain; His: Histidin-tagged
[3]SC: Santa Cruz Biotechnology, Inc., 89-2 Bergheimer Straße, 69120 Heidelberg, Tel. 49 (0)6221 4503 0, Toll Free +800 4573 8000, FAX 49 (0)6221 4503 45
[4]IV: Invitrogen GmbH, Technologiepark Karlsruhe, Emmy-Noether Strasse 10, 76131 Karlsruhe, Phone: 0800-0 83 09 02, FAX: 0800-0 83 34 35
[5]BD/Pharm: Becton Dickinson Biosciences (Pharmingen Products), Tullastrasse 8-12, 69126 Heidelberg, Germany, Tel: +(49) 6221.305.0, Fax: +(49) 6221.305.216,
[6]DIA: Dianova, Gesellschaft für biochemische, immunologische und mikrobiologische Diagnostik mbH, Mittelweg 176, D-20148 Hamburg, Tel.: 040/4 50 67-0, Fax: 040/4 50 67-490.
[7]see Schwabe, R. F., H. Engelmann, S. Hess, and H. Fricke. 1999. Soluble CD40 in the serum of healthy donors, patients with chronic renal failure, haemodialysis and chronic ambulatory peritoneal dialysis (CAPD) patients. Clin. Exp. Immunol. 117: 153.

Example 2

Comparison of TRAF Recruitment to CD40 in Intact Cells and in Cell Lysate.

Figure 2B:
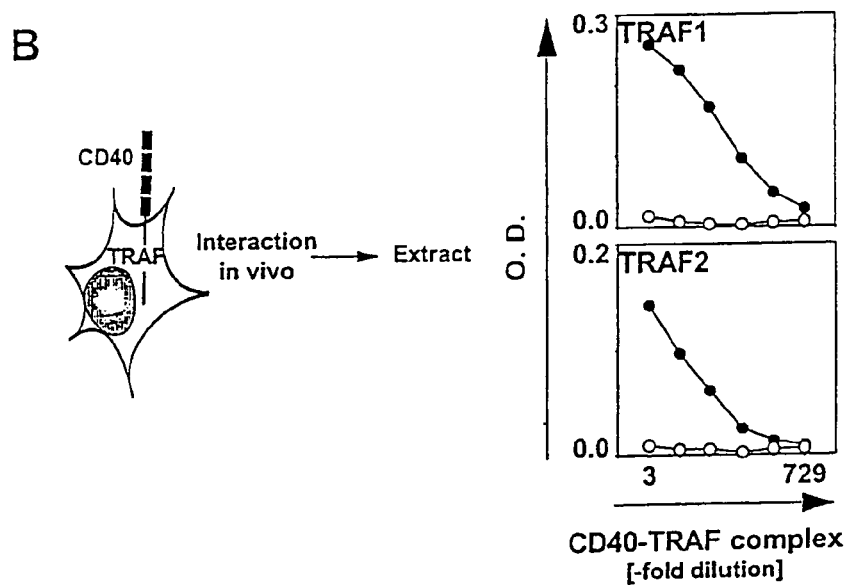

To measure TRAF recruitment to CD40 many studies relied on experimental systems that probe TRAF binding to synthetic peptides or soluble fragments of the CD40 signaling domain (Rothe et al. 1994, Hu et al. 1994, Cheng et al. 1995, Mosialos et al. 1995, Ishida et al. it 1996, Ishida et al. b 1996, Boucher et al. 1997, Pullen et al. 1998 and Pullen et al. 1999). A possible problem of these methods is that the signalosome assembly does not occur in the "juxta-membrane" environment. Therefore, recruitment of TRAF1 and TRAF2 by CD40 intact cells versus cell lysate was compared. In the experiment, CD40 and TRAF1 or TRAF2 were co-expressed or expressed separately in 293T cells (constructs described in example 7 below). Plasmid concentrations and ratios were identical to the experiment described in example 1. After 27 hours, the cells were detergent lysed as in example 1. The extracts from 293T cells expressing only CD40 or the TRAF of interest were mixed at a 1:1 ratio and incubated over night at 4° C. Extracts expressing both CD40 and the TRAF of interest were kept under identical conditions. Then the samples were incubated on microtiter plates coated with a mAb against the extra-cellular domain of CD40 as described in example 1. After a washing step, CD40 bound TRAFs were detected with anti TRAF antibodies (example 1). Quantitation of TRAF recruited to CD40 was carried out as described in the example 3 below. As seen in FIG. 2B the interaction between CD40 and TRAF1 or TRAF2 could be measured at clearly improved sensitivity when the assembly of the signalosome occurred in an intact cell while TRAF1 or TRAF2 binding to CD40 cell lysate was barely detectable (FIG. 2A).

The results suggest that effective TRAF recruitment requires the intracellular environment.

Example 3

Quantitation of TRAF Recruitment to CD40.

The recruitment of TRAF to CD40 can be quantitatively measured using the assay described in example 1. For that purpose, the assay conditions were adjusted in such a way that TRAF expression was in significant excess over the expression of CD40. This was the case when the TRAF expression plasmid was used at a two to three fold excess over the CD40 expression plasmid. The CD40 bound TRAF concentration was measured as described in example 1. A reference extract containing CD40/TRAF complexes served as a standard in each assay. This standard extract consisted of a large pool extract from cells that had been co-transfected with the plasmids encoding CD40/TRAF1, CD40/TRAF2, CD40/TRAF3, CD40/TRAF5 and CD40/TRAF6. The extracts were tested for the presence of CD40/TRAF complexes and the complex concentrations in each extract were arbitrarily defined as 1000 U/ml. The extracts were frozen in small aliquots and kept at −80° C. until further use. By comparing unknown samples to these extracts, it was possible to determine the relative CD40-TRAF complex concentrations in arbitrary units. The necessary normalization for sample-to-sample variations in the CD40 expression was calculated with the following formula:

$$\frac{\text{[receptor-recruited protein complex]}(arb. \text{ Units/ml})}{\text{[receptor concentration]}(ng/\text{ml})} = \text{receptor}$$

recruited protein complex per receptor protein ($arb$. Units/$ng$).

CD40 concentrations were determined with an ELISA employing a monoclonal antibody (solid phase) and a polyclonal anti CD40 antibody (for detection) both specific for the extracellular domain of the receptor. A purified soluble CD40 extra cellular domain was used as standard (Schwabe et al 1999).

Example 4

Re-evaluation of TRAF Recruitment to CD40 Mutants by the Assay Monitoring Recruitment in Intact Cells.

Sequence comparison, mutation analysis and crystallization studies mapped the two TRAF interaction sites in CD40 exhibiting the consensus sequences PxQET254 and QxPxE235x-acidic. Both TRAF binding motifs in CD40 were shown to mediate recruitment of TRAF1, 2, 3, 5 and 6 in vitro. Several binding studies demonstrated that TRAF6 binding depends essentially on the glutamic acid in position 235 (E235) (Pullen et al. 1999, Tsukamoto et al. 1999) and TRAF1, 2, 3 and 5 depends on the threonine in position 254 (T954) (Hu et al. 1994, Cheng et al. 1996, Boucher et al. 1997, Pullen et al. 1999, Hanissian et al. 1997) since their mutation to alanine resulted in complete loss of the corresponding TRAF binding. As mentioned herein, in order to measure TRAF recruitment to CD40 most studies had relied on experimental systems that probe TRAF binding to synthetic peptides or soluble fragments of the CD40 signaling domain.

Figure 3A:
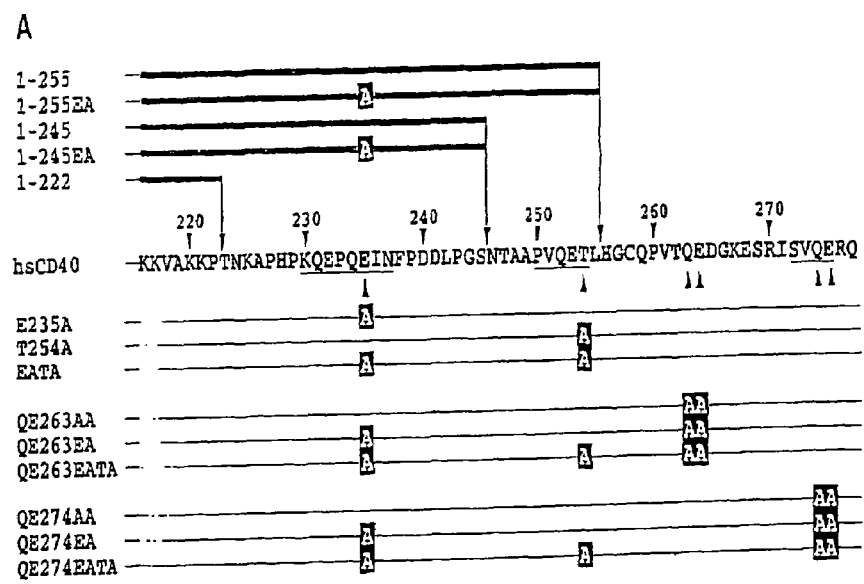
FIG. 3A is a schematic depiction of CD40 mutants tested for TRAF recruitment. The CD40 wild type sequence comprising the potential TRAF binding sites is shown in the middle (hsCD40 SEQ ID NO:1) with the two major TRAF binding sites underlined. A third sequence motif (SVQE) matching the consensus sequence for TRAF2 binding as determined by crystallization studies (Ye et al. 1999) is also underlined. Amino acids marked with an arrow were exchanged for an alanine (A).
Figure 3B:
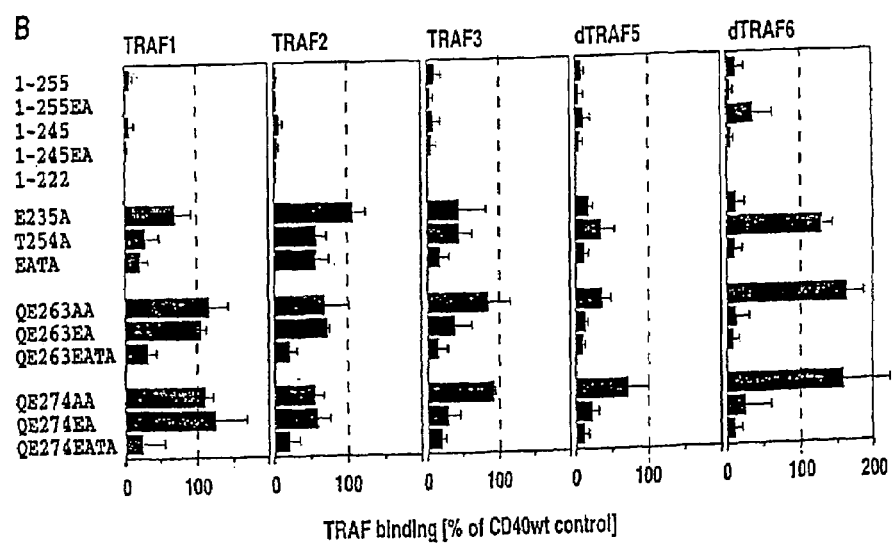
FIG. 3B shows TRAF recruitment to the CD40 mutants schematically represented in FIG. 3A. Shown is the relative TRAF binding to the mutant CD40 versus the wild type CD40 (as determined in the same experiment). All the determinations were done in three independent experiments in duplicates (shown are the means and variation around the mean value). For details on quantitation and normalization see example 3. The assays were done with the antibodies listed in Table 1. For determination of TRAF2 a monoclonal rat anti TRAF2 (clone 8.F1; kindly provided by Dr. E. Kremmer, GSF, Institut fuer Molekulare Immunologie; Marchioninistr. 25,81337 Munchen) was used as detection antibody (hybridoma supernatant diluted 1:10).

The quantitative version of the TRAF recruitment assay as described in example 3 was used to compare CD40 and various CD40 mutants with respect to their TRAF recruitment behaviour. TRAF 1, 2, 3, 5 and 6 were examined. CD40 mutants with deletions or point mutations in potential TRAF binding sites were used (FIG. 3A shows the potential TRAF binding site SEQ ID NO:1). As seen in FIG. 3B, the assay described here detected specific differences in TRAF recruitment depending on the CD40 mutant tested. Mutation of glutamic acid at position 235 (E235A) resulted in loss of TRAF6 recruitment. Additional deletion of the TRAF1/2/3/5 binding motif PXQXT254 at amino acid position 250 to 254 reduced the binding of all 5 TRAFs test to background levels (1-254EA in FIG. 3B). The assay also demonstrates that the C-terminus of CD40 (aa256 to aa277) is critical for the binding of all 5 TRAFs recruited by CD40 (1-255 in FIG. 3B). Furthermore it is shown that two TRAFs may influence each others recruitment. For example, the binding of TRAF6 was increased whenever a mutation was inserted in CD40 that lowered the binding of TRAF2 (for example T254A, QE263AA or QE274AA in FIG. 3B). Disablement of TRAF6 recruitment by the E235A mutation also led to reduced recruitment of TRAF3 and TRAF5 (FIG. 3B). An interesting side aspect came up when the CD40 mutant 1-245EA (in FIG. 3B) was tested for TRAF binding. Despite the presence of the consensus binding motif PXQE$^{231}$ for TRAF2 [as determined by crystallography (e et al. 1999)] in 1-254EA, this CD40 mutant did not bind TRAF2. This demonstrates that the sequence context in which the TRAF2 binding motif is situated also determines whether or not a given TRAF will be recruited.

The assay described here is clearly superior to previously used methods that detect the recruitment of TRAFs to CD40. Due to the use of the intact receptor in its natural membrane environment the sensitivity of this assay is clearly better than that of previously described methods (Rothe et al 1994, Hu et al. 1994, Boldin et al 1995, Stanger et al. 1995, Chinnaiyan et al. 1995, Cheng et al. 1995 Mosialos et al., 1995, Ishida et al. a 1996, Ishida et al. b 1996, Boucher et al. 1997, Pullen et al. 1998 and Pullen et al. 1999). Thus it is possible to detect CD40-TRAF interactions which could not be monitored before such as the binding of TRAF2 to the T254A mutant (Hu et al. 1994, Boucher et al. 1997, Pullen et al. 1999, Cheng et al. 1996, Hanissian et al. 1997) or the effect of the sequence environment on the consensus sequence for TRAF2 binding as determined in crystallization studies (Ye et al. 1999, NcWhirter et al. 1999 and Park et al. 1999). The assay allows a more precise determination of the structural requirements that determine TRAF binding to CD40 as for example the necessity of the intact CD40 C-terminus. Furthermore it was possible to demonstrate how different TRAFs affect each others binding. In view of these findings it is expected that the described assay method will contribute greatly to the understanding of the interaction between a cytokine receptor and intracellular signalling molecules. This knowledge will be essential for the rational development of drugs that act on the level of signalosome assembly.

Example 5

Recruitment of Various TRAFs to Different Receptors.

Figure 4A:
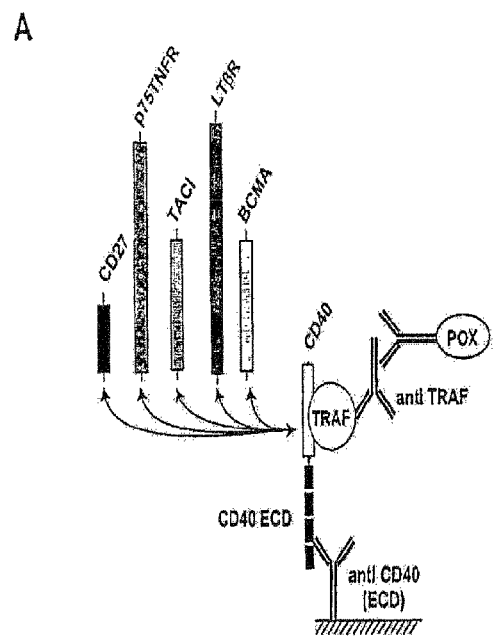
FIG. 4A is a schematic representation of the assay according to the invention for monitoring TRAF binding to different members of the TNF receptor family. Expression plasmids were constructed that code for receptor hybrids comprising a CD40 extra cellular domain and the transmembrane and intracellular domain of the receptor to be tested. TRAF recruitment to the signaling domains of CD27, the LTβ-receptor, the p75TNFR, TACI and BCMA known to recruit TRAF was carried out using the same assay as in example 1.
Figure 4B:
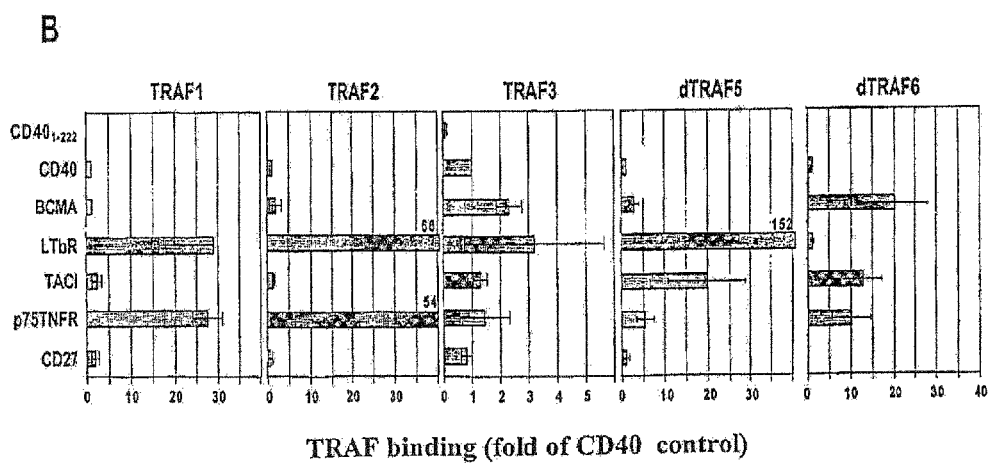
FIG. 4B shows the results obtained with the assay schematically represented and described in FIG. 4A. TRAF recruitment was determined as described in example 1 (for details on quantitation and normalization see example 3). Recruitment of TRAF to CD40 was used as the relative standard to compare the TRAF recruitment to the other tested receptors expressed as multiples of the reference CD40. The assay background was determined with a CD40 mutant lacking the entire signaling domain (CD40 1-222, see also FIG. 3). The assays were done with the antibodies listed in Table 1. For determination of TRAF2 a monoclonal rat anti TRAF2 (clone 8.F1; kindly provided by Dr. E. Kremmer, GSF, Institut fuer Molekulare Immunologie; Marchioninistr. 25,81337 Munchen) was used as detection antibody (hybridoma supernatant diluted 1:10).

Recruitment of various TRAFs to receptors different to CD40, was tested by the recruitment assay described in example 1 by transforming cells with expression plasmids encoding hybrids receptors comprising the extracellular domain of CD40 and transmembrane and intracellular domain of anyone of the following receptors: BCMA (Madry et al. 1998 and Hatzoglou et al. 2000) the LTβR-receptor (Mosialos et al. 1995, Crowe et al. 1994, Nakano et al. 1996), TACI (von Bulow et al. 1997, Xia et al. 2000) the p75TNFR (Rothe et al. 1994) and the CD27 (Gravestein et al. 1998, Akiba et al. 1998) (for details of constructs see example 7). Measurement of TRAF recruitment to the signalling domains of BCMA the LTβR-receptor TACI the p75TNFR or the CD27 was carried out by co-transfecting 293T cells with a plasmid encoding anyone of the above hybrid receptors together with a plasmid encoding TRAF and measurement of the TRAF/Receptor complex using the ELISA sandwich described in example 1 and the quantitation as described in example 3. The assay with the hybrid receptors is schematically represented in FIG. 4A. The results shown in FIG. 4B indicate that, using the assay monitoring recruitment in intact cells, any TRAF recruiting receptor of the TNF/NGF family can be examined with the same antibody sandwich assay described in example 1 and the amount of TRAF-receptor/CD40 hybrid complex can be monitored as described in example 3. The results show that recruitment of TRAF1 to LTβR and p75TN-FR is 25-folds higher than its recruitment to CD40, and that recruitment of TRAF2 to LTβR and p75TNFR is about 60-folds higher than its recruitment to CD40. Recruitment of TRAF3 to all the receptors tested is similar. TRAF5 is exceptionally highly recruited to LTβR, the recruitment to this receptor being about 152 folds higher than recruitment to the CD40 receptor. TRAF6 is recruited to BCMA, TACI and p75TNFR, about 10 fold higher than its recruitment to the CD40 receptor.

As seen in this example the assay described here allows for the firs time the direct comparison of several receptors with respect to their binding characteristics for a given set of signal molecules. This will make it possible to draw conclusions as to the biological functions of a given TRAF receptor combination. The results obtained demonstrate again the feasibility of the recruitment assay for monitoring TRAF recruitment to any receptor.

Example 6

Recruitment of NIK to CD40.

The assay described in example 1 can be used to measure recruitment of signal proteins, e.g. NIK (a downstream mediator in the NF-κB pathway Malinin et al. 1997) to a cytokine receptor, e.g. CD40 via an adaptor protein e.g. TRAF2. Expression plasmids encoding CD40, TRAF2, NIK (in pcDNA3.1) and myc-tagged IKKα were co-transfected into 293T (at a ratio of 1:1.75:1.75:1.75 respectively). Empty vector was used to equalize the amount of transfected DNA. The transfection was done as described for example 1. Twenty seven hours later the cells were extracted as described in example 1. The lysates were incubated with ELISA plates coated with an anti CD40 mAb (R01, Schwabe et al. 1997). After two hours the plates were washed with PBS/tween and developed with a commercially available rabbit anti NIK antibody (Santa Cruz at 1:100 dilution, SC-6363) and HRP-labeled goat anti rabbit Ig antibody (Pharmingen). The recruitment assay for NIK is schematically represented in FIG. 5A. As shown in FIGS. 5B and C, the recruitment of NIK to CD40 was TRAF2 dependent and clearly improved when IKK was co-expressed.

The results indicate that in addition to adaptor proteins, recruitment of other signalosome components such as NIK to the intracellular domain of the CD40 domain can be measured.

Example 7 cDNA Cloning, Generation of CD40 Mutants and Expression Constructs.

The human CD40 cDNA was cloned as described by Hess et al. (1995). CD40 cDNA was inserted in pEF-BOS (plasmid size 6164 bp).

The human TRAF2 cDNA was cloned as described by Mullinax et al., (1996). All other human TRAF cDNA were cloned by RT-PCR using the published sequence information.

Figure 6:
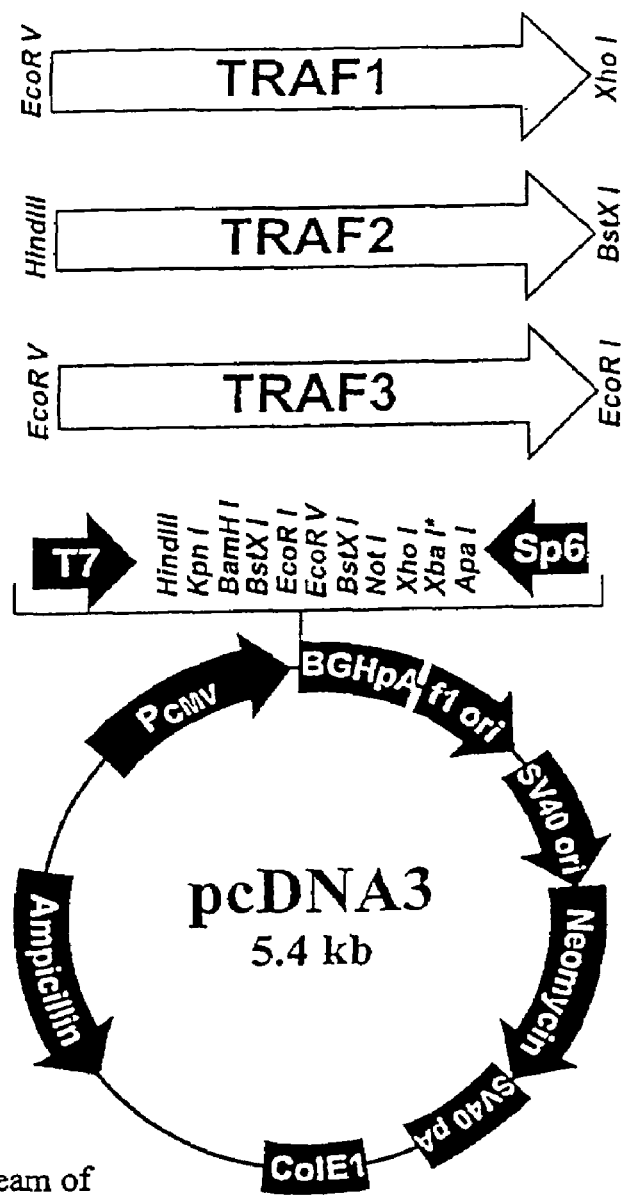
FIG. 6 shows the expression vectors encoding TRAF1, TRAF2 and TRAF3 (plasmid sizes are 6881, 7014, 7700 bp. For plasmids encoding TRAF1, TRAF2 and TRAF3 respectively).
Figure 7:
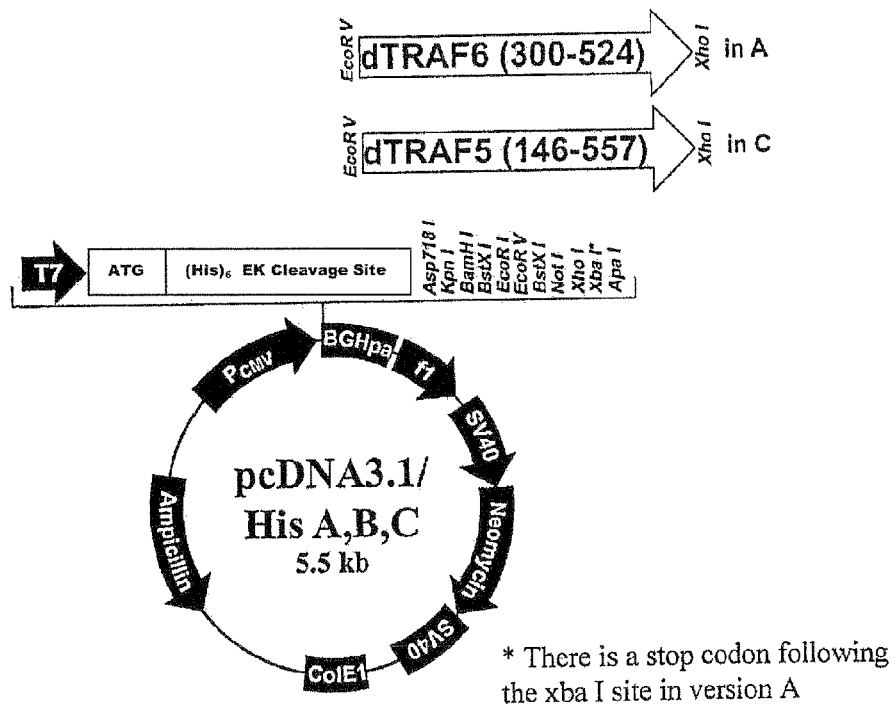
FIG. 7 shows the expression vectors encoding dTRAF5 and dTRAF6 (plasmid sizes are 6776 and 6199 bp for plasmids encoding dTRAF5 and dTRAF6 respectively). This expression vector codes for peptide tags enabling the detection with anti-His-tag or antiXpress antibodies. The cDNA fragments coding for deletion mutants of TRAF5 (dTRAF5) and TRAF6 (dTRAF6) were generated by enzymatic DNA restriction. Thus the NcoI to XhoI fragment coding for amino acids 145 to 557 of TRAF5 and XmnI to XhoI fragments coding for amino acids 300 to 524 of TRAF6 were used.

For expression of TRAF1, TRAF2 and TRAF3 the respective cDNAs were inserted in pcDNA3 (plasmid sizes are 6881, 7014 and 7700 bp for plasmids encoding TRAF1, TRAF2 and TRAF3 respectively) (FIG. 6). DTRAF5 and dTRAF6 were expressed in pcDNA3.1His (Invitrogen, Karlsruhe, Germany) and the plasmid size obtained were 6776 and 6199 bp for plasmids encoding dTRAF5 and dTRAF6 respectively. PcDNA3.1His vector codes for peptide tags enabling the detection with anti-His-tag or antiXpress antibodies (FIG. 7).

Figure 8:
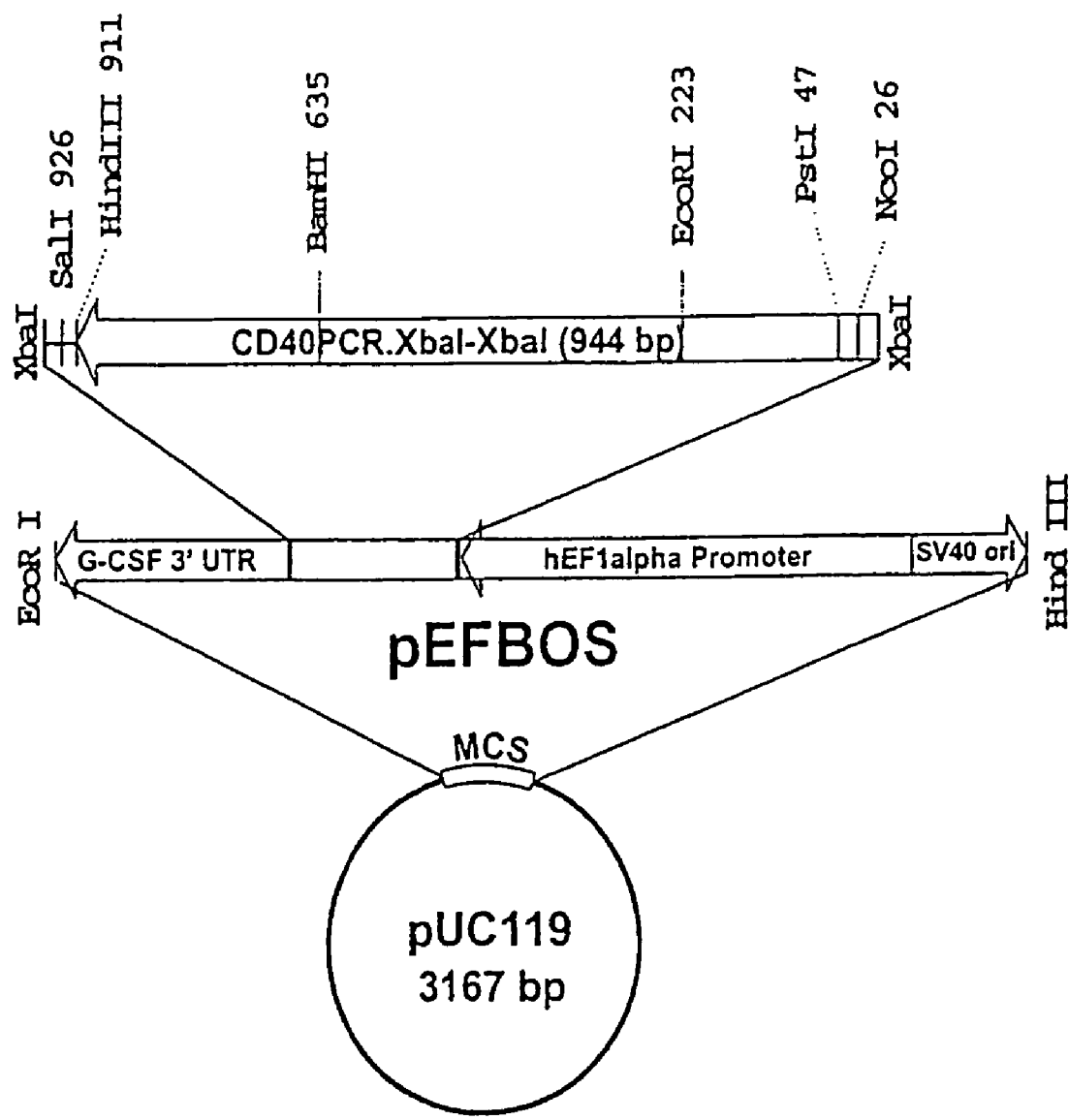
FIG. 8 shows expression vectors encoding CD40 mutants generated with the QuickChange™ Site directed Mutagenesis Kit (Stratagene, Netherlands) according to the manufacturer's induction. CD40 constructs were inserted in the Xba-1 site of pEF-BOS (Mizushima et al. 1990) and confirmed by sequencing.

The cDNA fragments coding for deletion mutants of TRAF5 (dTRAF5) and TRAF6 (dTRAF6) were generated by enzymatic DNA restriction. Thus the NcoI to XhoI fragment coding for amino acids 145 to 557 of TRAF5 and XmnI to XhoI fragments coding for amino acids 300 to 524 of TRAF6 were used (FIG. 8).

CD40 mutants were generated with the QuickChange™ Site directed Mutagenesis Kit (Stratagene, Netherlands) according to the manufacturer's induction. For expression all the CD40 constructs were inserted in the Xba-1 site of pEF-BOS (Mizushima et al. 1990) and confirmed by sequencing (FIG. 8).

Figure 9:
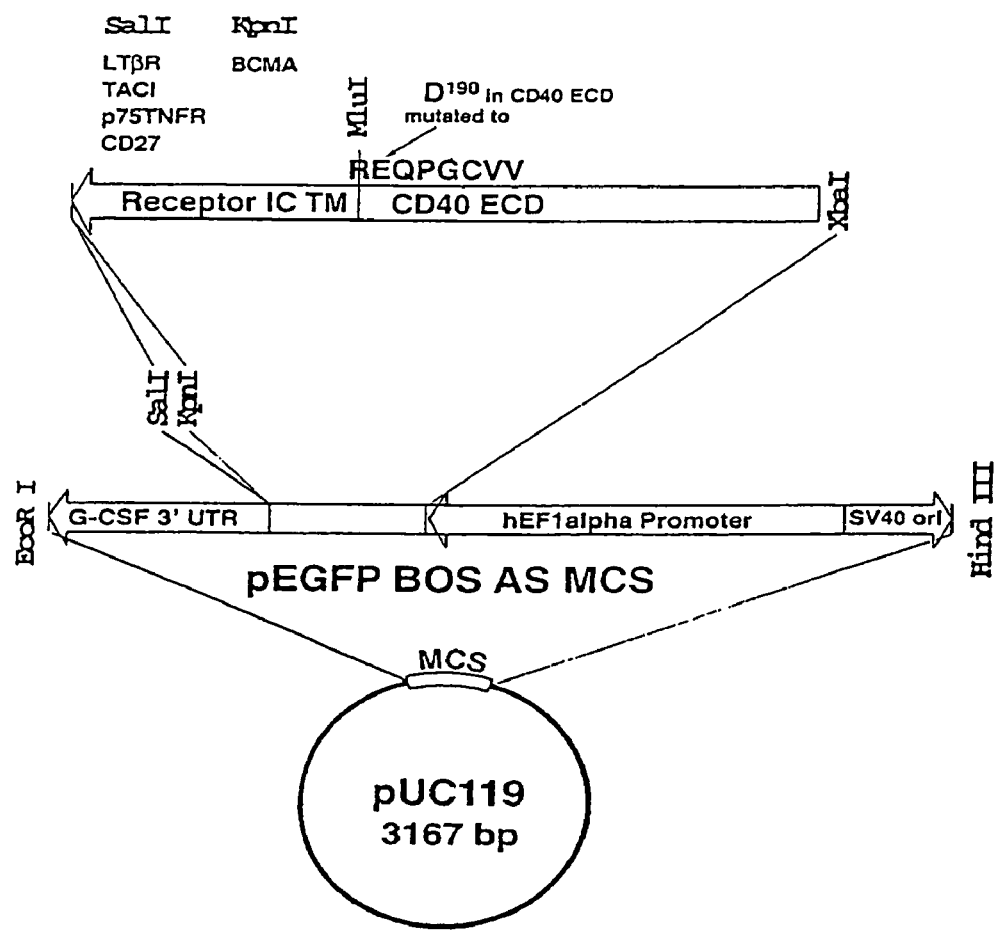
FIG. 9 DNA shows constructs encoding the hybrid receptors comprising the extracellular domain of CD40 and the intracellular and transmembrane domains of another receptor such as CD27, the LTβ-receptor, the p75TNFR, TACI and BCM in pUC119.

To generate the CD40 receptor hybrids the pEF-BOS variant pEGFP-BOS AS MCS was used (FIG. 9). This plasmid was generated by inserting the NheI-XbaI fragment obtained from the commercially available pEGFP-N1 plasmid (Clontech) in anti sense direction between the two XbaI sites in pEF-BOS. The fragment contained coding sequence for green fluorescent protein and the indicated restriction sites SalI and KpnI. PCR directed mutagenesis was used to create the unique MluI site at the extracellular to cytoplasmic domain border of the CD40 cDNA. This resulted also in the indicated mutation of aspartic (D) in position 190 to glutamic acid. Subsequently cDNA fragments encoding for the transmembrane and cytoplasmic domains of the LTβR, TACI, the p75TNF receptor, CD27 (all via SalI/MluI and of BCMA (via KpnI/MluI) were generated by PCR and inserted into pEGFP-BOS AS MCS together with the XbaI/mluI fragment encoding the CD40 extracellular domain (ECD). The indicated restriction sites in the cDNA fragments encoding the indicated receptor domains were generated by PCR directed mutagenesis and under the strict consideration that encoded amino acid sequence was identical to the corresponding wild type receptor. All constructs were reconfirmed by sequencing before use.

Example 8

Preparation and Screen of Non Peptide Small Molecules Inhibiting Signalosome Formation A library of small non peptide molecules are prepared by combinatorial chemistry. The design of combinatorial chemistry technology is well known in the art and is described e.g by Hermkens et al. (1996). Cells overexpressing CD40 and TRAF2 are exposed to individual synthetic organic compounds and recruitment is tested as described in example 1 and quantified as in example 3.

Compounds able to inhibit recruitment or signalosome formation are selected for future testing.

REFERENCES

Arch et al. 1998 Genes Dev. 12, 2821-2830.
Baud et al. 1999 Genes Dev. 13, 1297-1308.
Baeurle et al. 1994 Annu. Rev. Immunol. 12, 141-179.
Boldin M P et al. 1995 J Biol Chem April 7; 270(14): 7795-8
Boucher, L. M et al. 1997 Biochem. Biophys. Res. Commun. 233:592.
Brodeur et al. 1997 J. Biol. Chem. 272, 19777-19784.
Cheng, et al. 1995 Science 267:1494
Cheng et al. 1996 Genes Dev. 10, 963-973.
Chinnaiyan, et al. 1995. Cell 81: 505.
Clark et al. 1996 Adv. Immunol. 63, 43-78.
Darnay et al. 1999 J. Biol. Chem. 274, 7724-7731.
Devergne et al., 1996 Mol. Cell Biol. 16, 7098-7108.
DuBridge et al. 1987 Mol. Cell. Biol. 7:379.
Eliopoulos et al., 1997 Oncogene 14, 2899-2916.
Engelmann H et al. 1990. J. Biol Chem January 25; 265(3): 1531-6.
Engelmann H et al. 1990 J. Biol. Chem. 265, p. 14497-504.
Fields, S., and O. Song. 1989 Nature 340:245.
Foy et al. 1996 Annu. Rev. Immunol. 14, 591-617.
Gedrich et al. 1996 J. Pathol. 152, 1549-1561.
Ghosh et al. 1998 Annu. Rev. Immunol. 16, 225-663.
Grewal et al. 1998 Annu. Re. Immunol. 16, 111-135.
Hanissian et al. 1997 Immunobiology 178, 275-284.
Hu et al. 1994 J. Biol. Chem. 269 30069.
Inoue et al. 2000 Exp. Cell Res. 254, 14-24.

Ishida, et al. a 1996. Biol. Chem. 271:28745.
Ishida, et al. b 1996. Proc. Natl. Acad. Sci. V.S.A. 93:9437.
Karin et al. 1997 Curr. Opin. Cell. Biol. 9, 240-246.
Krajewska, et al. 1998. Am. J. Pathol. 152:1549.1561
Leo et al. 1999 J. Biol. Chem. 274, 22414-22422.
Liu et al. 1996 Cell 87, 565-576.
Lomaga et al. 1999 Genes Dev. 13, 1015-1024.
Malinin et al. 1997 Nature 385, 540-544.
Mizushima et al. 1990 Nucleic Acids Res. 18, 5322.
Naito et al. 1999 Genes Cells 4, 353-362.
Nakano et al. 1999 Proc. Natl. Acad. Sci. U.S.A. 96, 9803-9808.
McWhirter et al. 1999 Proc. Natl. Acad. Sci. U.S.A. 96, 8408-8413.
Mosialos, G et al. 1995 Cell 80:389.
Nguyen et al. 1999 Immunity 5, 407-415.
Ni et al. 2000 Proc. Natl. Acad. Sci. U.S.A 97, 10395-10399.
Park et al. 1999 Nature 398, 533-538.
Pullen, S. S et al. 1998. Biochemistry 37:11836.
Pullen, S. S. at al. 1999 J. Biol. Chem. 274:14246.
Ramesh et al. 1994 Immunol. Re. 138, 87-104.
Rothe et al. 1994. Cell 78:681.
Rothe et al. 1995 Cell 83, 1243-1252.
Sandberg et al. 1997 J. Virol. 71, 4649-4656.
Schonbeck et al. 2001 Cell Mol. Life Sci. 58, 4-43.
Shiels et al. 2000 Am. J. Pathol. 157, 679-688.
Song et al. 1997 Proc. Natl. Acad. Sci. U.S.A. 94, 9792-9796.
Stanger, et al. 1995 Cell 81:513
Takeuchi et al. 1996 J. Biol Chem 271, 19935-19942.
Tsukamoto et al. 1999 Proc. Natl. Sci. U.S.A. 96, 1234-1239.
Wallach, D et al. 1999 Annu Rev Immunol. 17, 331-67.
Xu et al. 1996 Immunity 5, 407-415.
Ye et al. 1999 Mol. Cell 4, 321-330.
Yeh at al. 1997 Biochemistry 38, 10168-10177.

c) incubating the cell lysate on a solid phase coated with a first antibody capable of capturing the receptor within the signalosome;
d) separating the solid phase from the cell lysate; and
e) detecting and measuring the amount of a protein component of the signalosome using a second antibody capable of detecting the protein to monitor the binding of the protein to the intracellular domain of the receptor as part of the intact signalosome,
wherein the signalosome remains intact and bound to the solid phase of c) during detecting and measuring.

2. A method according to claim 1, wherein signalosome formation is induced by receptor overexpression.

3. A method according to claim 1, wherein signalosome formation is induced by receptor activation.

4. A method according claim 3, wherein receptor activation is induced by treating the cell with a ligand to the receptor.

5. A method according to claim 4, wherein receptor activation is induced by receptor cross-linking.

6. A method according to claim 5, wherein cross-linking is induced by a receptor specific antibody.

7. A method according to claim 1, wherein the receptor is selected from the group consisting of CD40, BCMA, LTβR-receptor, TACI, p75TNFR and CD27.

8. A method according to claim 1, wherein the protein bound to the solid phase as part of the still intact signalosome is an adaptor protein selected from the group consisting of TRAF1, TRAF2, TRAM, TRAF4, TRAF5 and TRAF6.

9. A method according to claim 1, wherein the protein bound to the solid phase as part of the still intact signalosome is an enzyme.

10. A method according, to claim 9, wherein the Enzyme is a kinase.

The invention claimed is:

1. A method for monitoring binding of a protein to the intracellular domain of a receptor in a cell, comprising:
a) inducing signalosome formation in cells, wherein the signalosome is a multi-protein complex comprising a receptor, one or more adaptor proteins and one or more signaling proteins, and the signalosome forms in the intact natural cellular environment within the cell;
b) lysing the cells;

11. A method according to claim 10, wherein the kinase is NIK.

12. A method according to claim 1, wherein the protein bound to the solid phase is IKK.

13. A method according to claim 1, wherein the receptor is fused to a polypeptide or peptide at its extracellular domain and wherein the first antibody is specific for such fused polypeptide or peptide.

14. A method according to claim 13, wherein the fused peptide is a specific Tag and wherein the first antibody is specific for such a tag.

15. A method according to claim 13, wherein the polypeptide is the extracellular domain of a receptor and wherein the first antibody is specific for such extracellular domain.

16. A method according to claim 15, wherein the fused polypeptide is the extracellular domain of CD40.

17. A method according to claim 1, wherein the protein bound to the solid phase is fused to a tag and wherein the second antibody is specific for such a tag.

18. A method according to claim 17, wherein the tag is selected from histidine, FLAG, VSV-G, Protein-C and c-myc tags.

19. A method for screening for molecules which inhibit the binding of an adaptor protein and/or signaling protein to an intracellular domain of a receptor in a cell comprising:
   exposing the cells to individual molecules, monitoring binding of a protein to the intracellular domain of a receptor with a method according to claim 1 and selecting a molecule capable of inhibiting the binding of the adaptor and/or signalling protein to the receptor.

20. A method according to claim 19, wherein the screened molecules are synthetic organic compounds.

21. A method for screening for molecules that inhibit signalosome assembly in a cell comprising:
   a) inducing signalosome formation in a cell, wherein the signalosome is a multi-protein complex comprising a receptor, one or more adaptor proteins and one or more signaling proteins, and the signalosome forms in the intact natural cellular environment within the cell;
   b) exposing the cells to individual generated molecules;
   c) lysing the cell;
   d) incubating the cell lysate on a solid phase coated with a first antibody capable of capturing the receptor within the still intact signalosome;
   e) separating the solid phase from the cell lysate;
   f) detecting and measuring the amount of signalosome formed and bound to the solid phase using a second antibody capable of detecting any one of the sigmalosome components except the receptor that is bound to the solid phase; and
   g) selecting a molecule capable of inhibiting signalosome formation.

22. A method according to claim 21, wherein signalosome formation is induced by overexpression of several or all of the signalosome components.

23. A method according to claim 21, wherein signalosome formation is induced by receptor activation.

24. A method according claim 23, wherein receptor activation is induced by treatment of the cell with the ligand to the receptor.

25. A method according to claim 23, wherein receptor activation is induced by receptor cross-linking.

26. A method according to claim 25, wherein cross-linking is induced by a receptor specific antibody.

27. A method according to claim 21, wherein the receptor within the signalosome is selected from the group consisting of CD40, BCMA, LTβR-receptor, TACI, p75TNFR and CD27.

28. A method according to claim 21, wherein the signalosome component measured, which is different from the receptor, is an adaptor protein selected from the group consisting of TRAF1, TRAF2, TRAM, TRAF4, TRAF5, and TRAF6.

29. A method according to claim 21, wherein the component monitored in the signalosome which is different from the receptor is an enzyme.

30. A method according to claim 29, wherein the enzyme is a kinase.

31. A method according to claim 30, wherein the kinase is NIK.

32. A method according to claim 21, wherein the signalosome component measured, which is different from the receptor, is IKK.

33. A method according to claim 21, wherein the receptor within the signalosome is fused to a peptide or polypeptide at its extracellular domain and wherein the first antibody is specific for such fused peptide or polypeptide.

34. A method according to claim 33, wherein the polypeptide is a specific Tag.

35. A method according to claim 33, wherein the fused polypeptide, is the extracellular domain of a receptor.

36. A method according to claim 35, wherein the fused polypeptide is the extracellular domain of CD40.

37. A method according to claim 21, wherein the signalosome component measured, which is different from the receptor, is fused to a tag and wherein the second antibody is specific to such a tag.

38. A method according to claim 37, wherein the tag is selected from histidine, FLAG, VSV-G, Protein-C and c-myc tags.

39. A method according to claim 21, wherein the screened molecule is a synthetic organic compound.

40. A method for screening for molecules which inhibit the binding of an adaptor protein and/or signaling protein to an intracellular domain of a receptor in a cell comprising:
   monitoring binding of a protein to the intracellular domain of a receptor according to claim 1 in transfected cells exposed to individual molecules using a kit for measuring and quantitating binding of an adaptor and/or signalling protein to a specific membrane protein in a cell which comprises:
   a) two expression plasmids, one for overexpressing the membrane protein fused to a first tag or polypeptide, and the other plasmid for expressing of an adaptor/signalling protein fused to a second tag;
   b) ELISA microtiter plates coated with a first antibody capable of binding the first tag or polypeptide fused to the membrane protein;
   c) a second antibody capable of binding a second tag fused to the adaptor/signalling protein;
   d) Transfection reagents;
   e) Lysis buffer;
   f) a protocol describing concentration of vectors in the transfection reaction, and concentration of antibodies in the ELISA and way of quantitation; and
   selecting a molecule capable of inhibiting the binding of the adaptor protein and/or signalling protein to the receptor.

41. A method according to claim 40, wherein the screened molecule is a synthetic organic compound.

* * * * *

SEQUENCE LISTING

```
<160> NUMBER OF SEQ ID NOS: 1

<210> SEQ ID NO 1
<211> LENGTH: 62
<212> TYPE: PRT
<213> ORGANISM: Homo sapiens

<400> SEQUENCE: 1

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60
```